United States Patent [19]
Shoemaker

[11] Patent Number: 5,725,532
[45] Date of Patent: Mar. 10, 1998

[54] INTEGRATED SURGICAL REDUCTION CLAMP AND DRILL GUIDE

[76] Inventor: Steven Shoemaker, 2226 Thurton Dr., Roseville, Calif. 95747

[21] Appl. No.: 711,274

[22] Filed: Sep. 10, 1996

[51] Int. Cl.⁶ .......................... A61B 17/90; A61B 17/28
[52] U.S. Cl. .......................... 606/96; 606/104; 606/207
[58] Field of Search .................. 606/96, 104, 205, 606/206, 207, 174

[56] References Cited

U.S. PATENT DOCUMENTS

| | | | |
|---|---|---|---|
| 2,181,746 | 11/1939 | Siebrandt | 128/83 |
| 2,887,111 | 5/1959 | Diaz | 606/148 |
| 4,235,428 | 11/1980 | Davis | 269/53 |
| 4,312,337 | 1/1982 | Donohue | 128/92 EB |
| 4,444,180 | 4/1984 | Schneider et al. | 128/92 EB |
| 5,026,376 | 6/1991 | Greenberg | 606/96 |
| 5,154,720 | 10/1992 | Trott et al. | 606/96 |

Primary Examiner—Michael Buiz
Assistant Examiner—David O. Reip
Attorney, Agent, or Firm—Bradley P. Heisler

[57] ABSTRACT

A non-opposed surgical reduction clamp 10 is provided which has a drill guide 40 integrally formed with a guide leg 20 of the reduction clamp 10. The reduction clamp 10 also includes a reference leg 50 pivotably connected to the guide leg 20 through a pivot 70. The reference leg 50 includes a sharpened tip 57 at a tip thereof which can penetrate into a surface of a bone somewhat to prevent slippage of the reference leg 50. The drill guide 40 has an inner cylindrical surface 44 to provide an alignment axis Z for location of bone fixation structures, such as K-wire, pins or screws for reattachment and fixation of fractured bone fragments. Alignment axis Z of the drill guide 40 is in a common plane with the sharpened tip 57 of the reference leg 50, but extends beyond the sharpened tip 57 of the reference leg 50. Ends of the reference leg 50 and guide leg 20 opposite the sharpened tip 57 and drill guide 40 are provided with handle loops 30, 60 and clamp tabs 32, 62 to allow the reduction clamp 10 to be easily manipulated by a surgeon and clamped into position. The reduction clamp 10 is particularly configured to provide for reattachment of a lower tip H of a tibia T and to reattach a lower end E of a fibula F within the ankle A of a human patient. Precise orientation of the bone fixation structures such as wire K is provided without requiring a fully opposed reduction clamp.

18 Claims, 3 Drawing Sheets

INTEGRATED SURGICAL REDUCTION CLAMP AND DRILL GUIDE

FIELD OF THE INVENTION

The following invention relates to reduction clamps for holding bone fragments together during orthopedic bone fracture repair surgery, and particularly reduction clamps which include a drill guide for alignment of a drill to be used in the fracture repair surgery. More specifically, this invention relates to reduction clamps with included drill guides that can be used in a non-opposing manner in surgical sites where an opposing reduction clamp cannot be used.

BACKGROUND OF THE INVENTION

As advances have been made in orthopedic bone fracture repair surgery, bone reattachment and support structures such as plates, pins, screws and wires have become widely used. Such bone reattachment structures have allowed for the reconstruction and complete repair of severely fractured and shattered bones.

To effectively perform such a surgery, it is critical that the bone fragments be precisely located and held in place and that the fixation utilized be placed in the bone to effectively place the bone where desired. To facilitate holding of bone fragments in place during such fracture repair surgery, reduction clamps are often used. Such reduction clamps are generally configured as a scissors-like object with a pair of jaws which oppose each other. The jaws are spaced apart a sufficient distance to allow them to be oriented on opposite sides of two bone fragments opposite a fracture line there between so the two fragments can be drawn together and held in intimate contact by the opposing jaws of the reduction clamp.

To provide for accurate placement of the bone fastener, drill guides are known which are configured generally as a hollow cylindrical guide tube connected to a support arm. The cylindrical tube and support arm are precisely located where desired and then held in place, such as with a hand of the surgeon or other medical professional. The rotating tip of the drill is then passed through the hollow cylinder to align the drill and then a rotating tip attached to the drill penetrates into the bone where desired.

While such reduction clamps and drill guides are generally effective in some surgeries, their use has not been entirely satisfactory for many surgeries. Also, because both the reduction clamp and drill guide must both be carefully held in position, the surgical process typically requires multiple medical professionals to be accurately performed. More recently, some reduction clamps have been modified to include a drill guide integrally formed with the reduction clamp so that both the bone fragment holding function and the drill alignment function can be performed with a single tool. For instance, U.S. Pat. No. 2,181,746 to Siebrandt and U.S. Pat. No. 4,444,180 to Schneider both teach surgical reduction clamps which include a drill guide formed therewith.

Many surgeries where bone fragments need to be drawn together and held in place and where drill guides are required to accurately orient a drill are necessary at surgical sites where an opposing reduction clamp cannot be utilized. In such surgical environments, opposing reduction clamps such as the Siebrandt device and the Schneider device are not effective. For instance, when ankle reconstruction surgery is required because lower tips of the tibia and/or fibula have been fractured, it is required that bone fragments be held against the lower end of the tibia or fibula. At such surgical sites no opposing surface is provided around which both of the jaws of a prior-art opposing reduction clamp can be located. To utilize prior art reduction clamps at such sites would damage the joint further For such surgeries, it is the state of the prior an to utilize a drill guide alone and possibly hold the bone fragments in place manually during the drilling process. In practice, many such fractures involving the lower tip of the tibia or fibula may not be effectively repaired and the patient's use and functionality of their ankle is diminished somewhat as a result of the imperfect repair of the ankle fracture.

Accordingly, a need exists for a combined reduction clamp and drill guide which is non-opposing. Such a clamp could be used in orthopedic bone fracture repair surgeries where opposing reduction clamps cannot be used, such as to repair fractures which commonly occur at the lower end of the tibia and fibula of a human ankle or other periarticular fractures.

SUMMARY OF THE INVENTION

This invention provides a non-opposing reduction clamp capable of both holding fractured bone fragments in position for reattachment and simultaneously providing a drill guide for alignment of the drill and bone fixation structures such as pins, screws, wires and the like. The reduction clamp of this invention is generally "scissors-like" with a guide leg and a reference leg pivotably attached together. Both the guide leg and reference leg include a handle loop at handle ends thereof and clamping means there between such as two damp tabs with clamp teeth thereon which extend toward each other and can lock together.

An end of the guide leg opposite the handle loop includes a drill guide thereon. The drill guide is generally a hollow cylindrical tube which is sized to allow rotating portions of the drill and bone reattachment structures to be supported while passing through the tube. The end of the reference leg opposite the handle loop includes a tip which is sharpened and can penetrate into one of the bone fragments somewhat to prevent sliding of the reduction clamp when in use. The sharpened tip does not point toward the drill guide and so provides no opposition to the drill guide and guide leg. The length of the reference leg and the orientation of the drill guide central axis are such that the drill is always oriented along an alignment axis which is in a common plane with the reference leg but passes beyond the tip of the reference leg. Thus, the reduction clamp always directs the bone fixation structure extending through the drill guide to a position beyond the reference leg. When the sharpened tip of the reference leg is adjacent a surface of a bone fragment, this separation between the alignment axis and the tip ensures that the bone reattachment structure will remain embedded within the bone fragment at the region adjacent the tip of the reference leg. Angles of orientation for the drill guide and other portions of the reduction clamp are particularly configured to provide the drill guide with an orientation which locates the bone fixation structure precisely where desired. Thus, the reduction clamp provides for consistent and superior surgical results when compared to prior art techniques, and is used in situations where prior art techniques cannot be used.

OBJECTS OF THE INVENTION

Accordingly, the primary object of the present invention is to provide a surgical reduction clamp which includes a drill guide integrally formed therewith and which can be used in an environment where an opposing reduction clamp cannot be used.

Another object of the present invention is to provide a surgical reduction clamp which can simultaneously hold fractured portions of a bone together and align a drill for insertion of a bone fixation structure through the bone fragments to reconnect the bone fragments together.

Another object of the present invention is to provide a surgical reduction clamp and drill guide which can be operated with a single hand of a user, leaving a second hand free for other activities such as operation of a drill.

Another object of the present invention is to provide a surgical reduction clamp which can be utilized to repair fractures at the lower tip of the tibia and the lower end of the fibula or other boney outcroppings with bone fixations such as wire, pins or screws.

Another object of the present invention is to provide a surgical reduction clamp which is configured in a simple manner to allow it to be readily used with a minimal amount of training in its use required.

Another object of the present invention is to provide a surgical reduction clamp which is of a simple construction and can be formed from relatively low cost materials, and yet provides highly accurate, reliable and consistent results.

Another object of the present invention is to provide a surgical reduction clamp which includes a drill guide which is angled at a precise angle for accurate placement of bone reattachment structures at a desired position within the bones to be reattached.

Another object of the present invention is to provide a method for repairing a bone fracture which utilizes a surgical reduction clamp with a drill guide integrally formed therewith and which can be used in surgical environments where bone surfaces parallel to the fracture are not available for an opposing reduction clamp.

Other further objects of this invention will become apparent from a careful reading of the included description, and claims as well as a careful review of the included drawing figures.

BRIEF DESCRIPTION OF THE DRAWING FIGURES

DESCRIPTION OF THE PREFERRED EMBODIMENT

Figure 1:
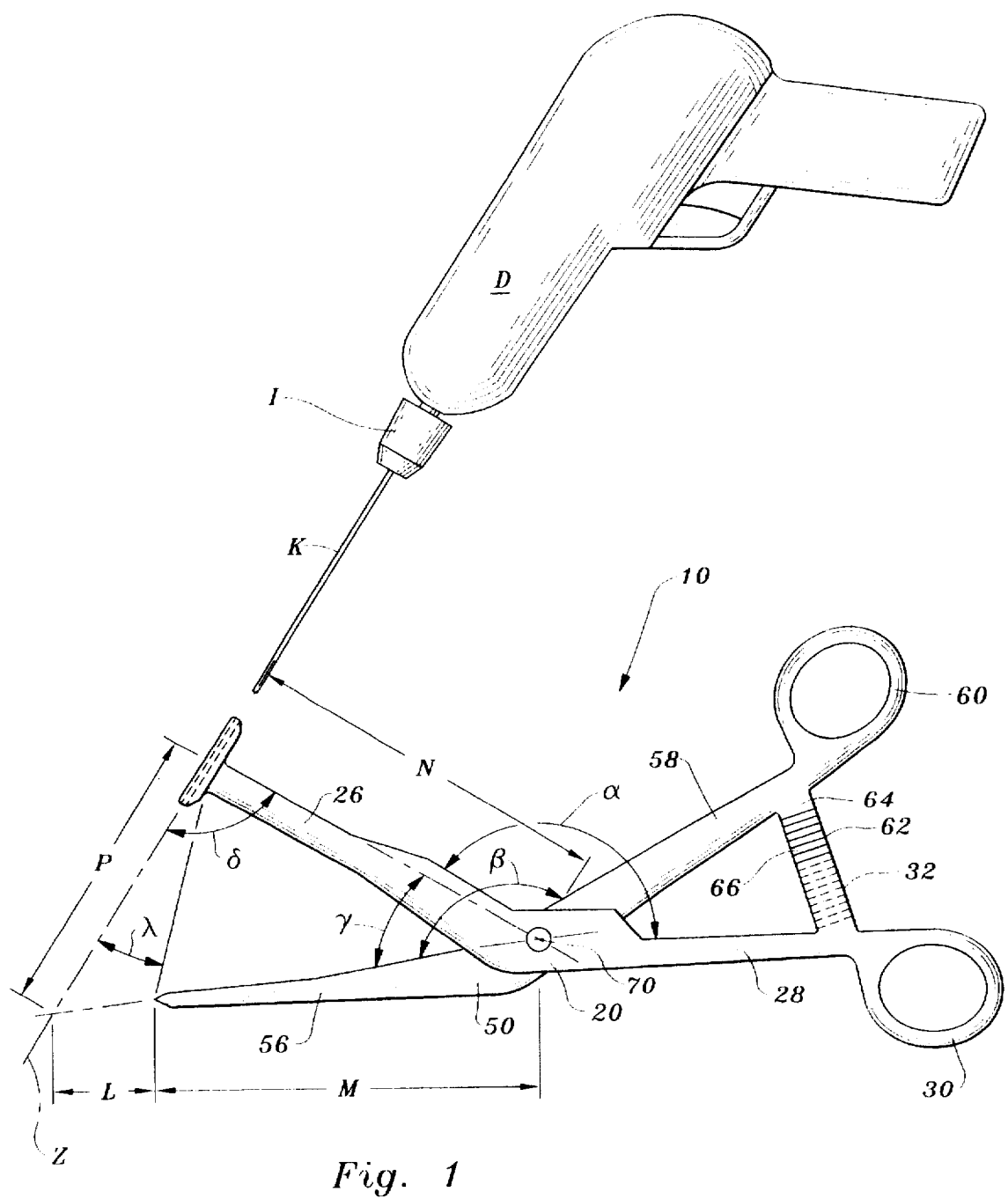
FIG. 1 is a front elevation view of the integrated surgical reduction clamp and drill guide of this invention shown along with a drill.
Figure 4:
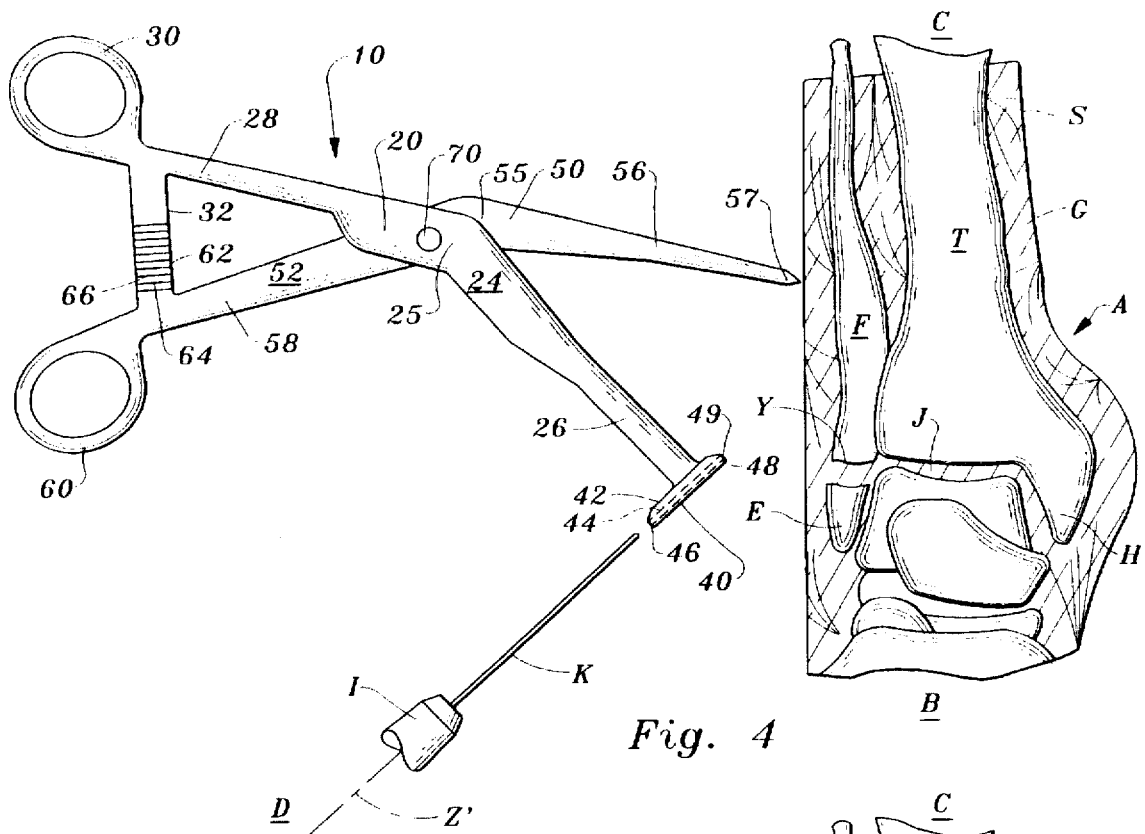
FIG. 4 is a front elevation view of the reduction clamp of this invention in an orientation just prior to its use in repairing a fracture of the lower end of the fibula of a human patient.
Figure 5:
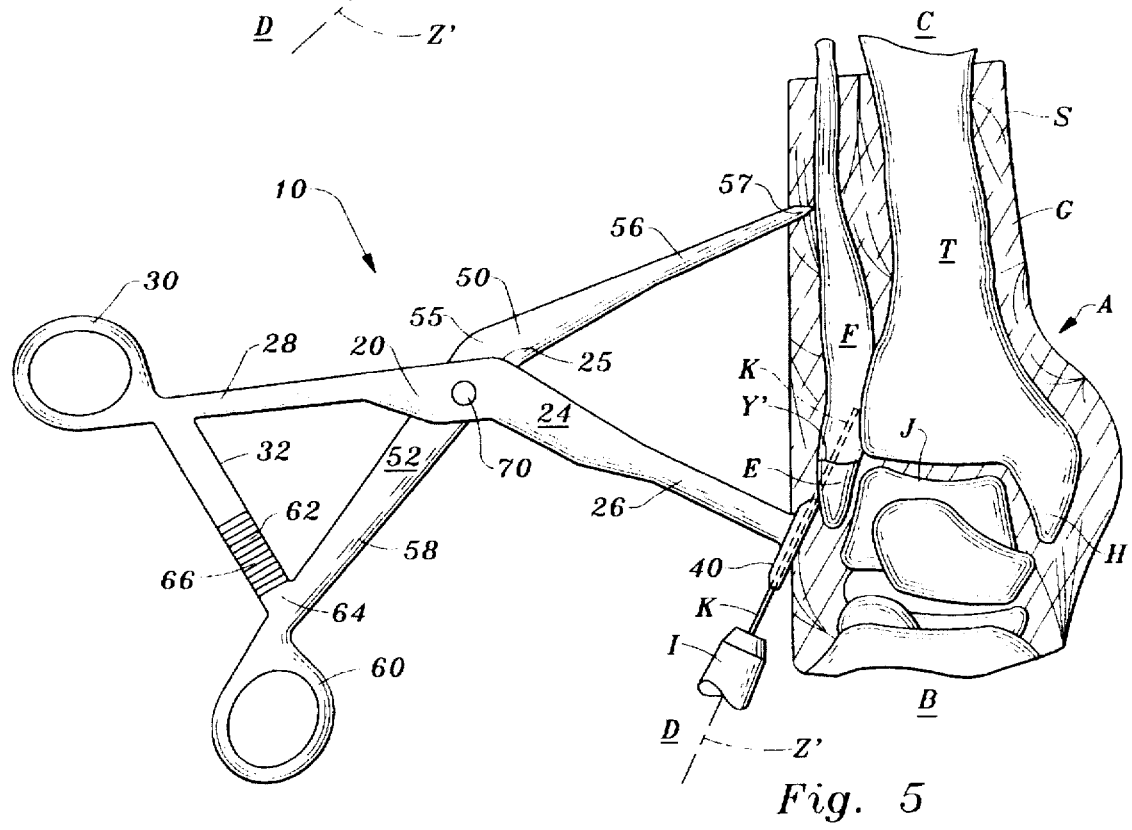
FIG. 5 is a front elevation view of that which is shown in FIG. 4 with the reduction clamp of this invention precisely positioned and in use repairing the lower end of the fibula of the patient.

With reference to the drawings, wherein like reference numerals represent like parts throughout, reference numeral 10 is directed to an integrated surgical reduction clamp and drill guide (FIG. 1). The reduction clamp 10 is generally "scissors-like" in configuration with a guide leg 20 and reference leg 50 pivotably connected together at a pivot 70. The reduction clamp 10 can be used to repair bone fractures such as fractures X which occur at a lower tip H of a tibia T (FIGS. 2 and 3) or fractures Y at the lower end E of the fibula F (FIGS. 4 and 5). The reduction clamp includes a drill guide 40 through which a bone fixation structure such as a wire K or a drill bit can be aligned while rotated by a drill D (FIG. 1).

In essence, and with particular reference to FIG. 1, the reduction clamp 10 has the following basic structure. The guide leg 20 and reference leg 50 are coupled together at the pivot 70 which is approximately medially located along the guide leg 20 and reference leg 50. The guide leg 20 includes a guide end 26 on one side of the pivot 70 and a handle end 28 on the other side of the pivot 70. The drill guide 40 (FIG. 2) is located at the tip of the guide end 26 of the guide leg 20. A handle loop 30 is oriented on the handle end 28 of the guide leg 20. The reference leg 50 has a reference end 56 on one side of the pivot 70 and a handle end 58 on the other side of the pivot 70. A sharpened tip 57 (FIG. 2) is oriented at the end of the reference end 56. A handle loop 60 is oriented at the end of the handle end 58. The sharpened tip 57 of the reference leg 50 and the drill guide 40 of the guide leg 20 are utilized adjacent the patient during the surgical procedure while the handle loops 30, 60 are held by the medical professional to position the reduction clamp 10 where desired for performance of the surgical procedure. The medical professional can manipulate the relative orientation of the sharpened tip 57 and the drill guide 40 by pivoting the guide leg 20 and reference leg 50 about the pivot 70, through use of the medical professional's fingers adjacent the handle loops 30, 60.

More specifically, and with particular reference to FIGS. 1 and 4–5, details of the guide leg 20 of the reduction clamp 10 are provided. The guide leg 20 is preferably an elongate rigid structure formed from a material such as stainless steel or other sterilizable materials. The guide leg 20 has an inner surface 22 (FIGS. 2 and 3) which is parallel to and spaced from an outer surface 24. The guide leg 20, while generally linear and elongate, has a bend 25 at a medial location thereof. The bend 25 exhibits a bend angle $\alpha$ which preferably measures 150°.

The guide leg 20 includes a guide end 26 on one end of the bend 25 and a handle end 28 on the other end of the bend 25. The two ends 26, 28 are generally linear and diverge from each other by the bend angle $\alpha$. Preferably, the guide leg 20 exhibits an increased width adjacent the bend 25 to increase a structural strength of the guide leg 20 adjacent the bend 25. The pivot 70 attaches the guide leg 20 to the reference leg 50 near the bend 25.

A handle loop 30 is oriented at a tip of the handle end 28. The handle loop 30 is generally circular and is sized to allow a thumb or fingers of a medical professional to pass through an interior thereof for manipulation of the guide leg 20. A first clamp tap 32 is oriented near the tip of the handle end 28 and extends obliquely, but substantially perpendicularly away from the handle end 28 of the guide leg 20. The first clamp tab 32 extends toward the reference leg 50. The first clamp tap 32 includes a series of clamp teeth 36 (FIGS. 2 and 3) on an interior surface 34. The interior surface is parallel to and faces in a common direction with the inner surface 22 of the guide leg 20. The teeth 36 are preferably biased so that they can lock with clamp teeth 66 (FIGS. 4 and 5) of a second clamp tab 62 of the reference leg 50, to be described below.

The drill guide 40 is affixed to the tip of the guide end 26 of the guide leg 20. Thus, the drill guide 40 is on an end of the guide leg 20 distant from the handle loop 30. The drill guide 40 provides a means to guide the orientation of the drill and the orientation of any bone reattachment structures along an alignment axis Z which is oriented as desired for location of the bone reattachment structure within the bone fragments of the patient.

Preferably, the drill guide 40 is a hollow cylindrical rigid construct with an outer cylindrical surface 42 parallel to and spaced from an inner cylindrical surface 44. The hollow interior of the drill guide 40 forms a bore which passes from an inlet end 46 to an outlet end 48. The outer cylindrical surface 42 is rigidly attached to the guide end 26 of the guide leg 20. The inner cylindrical surface 44 has a constant circular cross-section and is sized to be not less than a diameter of the bone reattachment structure which is oriented there through or a drill bit which may be oriented there through to provide a hole passing through the bone fragments to be reattached.

Preferably, the drill guide 40 is not centered upon the tip of the guide end 26, but rather is oriented such that the outlet end 48 is closer to the tip of the guide end 26 than it is the inlet end 46. In this way, an overall length of the drill guide 40 from the inlet end 46 to the outlet end 48 can be enhanced while the outlet end 48 is maintained close to the guide end 26 of the guide leg 20, for precise location of the outlet end 48 where desired by the medical professional.

Preferably, the outlet end 48 of the drill guide 40 is configured with a sharpened rim 49. This sharpened rim 49 has sufficient sharpness that it can penetrate slightly into bones of the patient such as the tibia T or fibula F slightly. In this way, the drill guide 40 is prevented from sliding away from a desired position upon the tibia T or fibula F. The sharpened rim 49 preferably circumscribes the outlet end 48 of the drill guide 40. Alternatively, the sharpened rim 49 can be provided as a crescent around only part of the outlet end 48 or as a series of spikes or other traction features adjacent the outlet end 48 to provide for added friction between the drill guide 40 and the bone fragments adjacent thereto.

Figure 2:
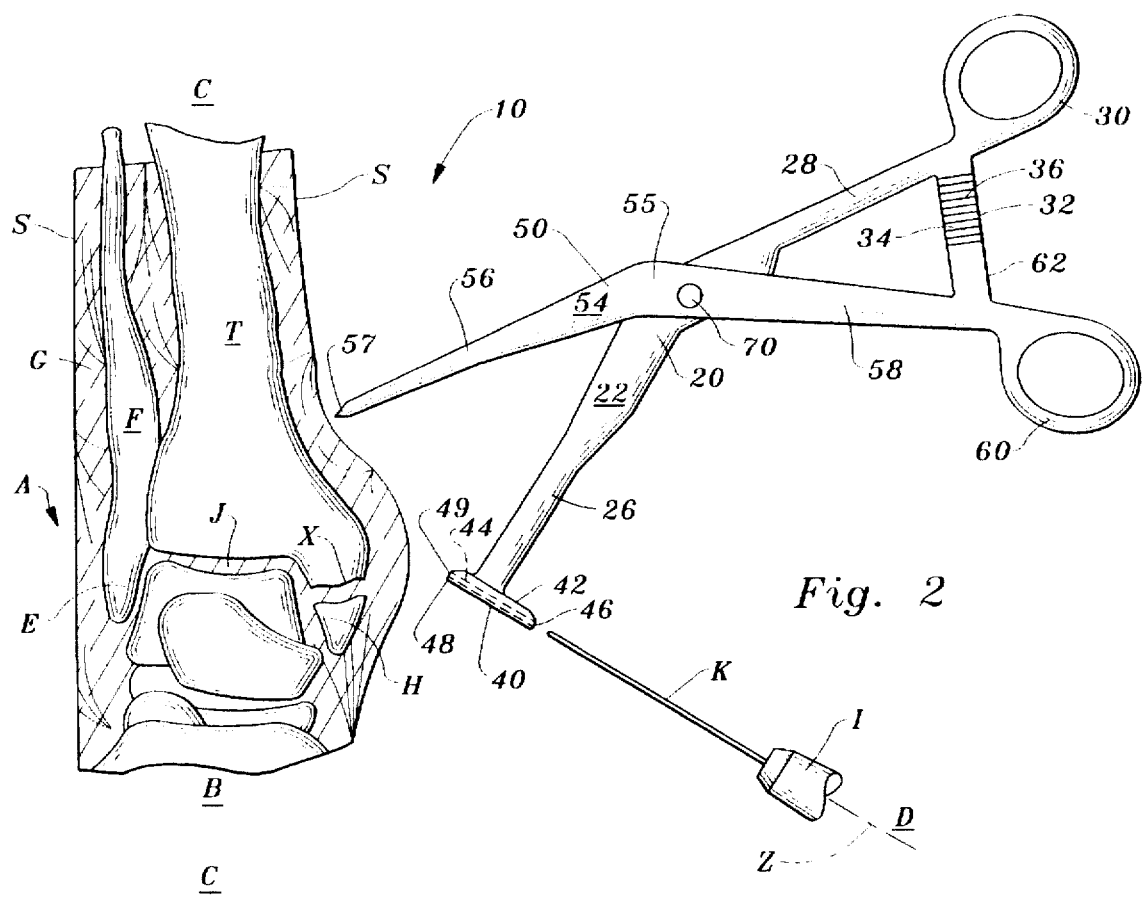
FIG. 2 is a front elevation view of the surgical reduction clamp of this invention just prior to its use in repairing the lower tip of the tibia of a human ankle, the ankle of the patient shown in partial section to reveal interior details of the bone structures to be repaired.
Figure 3:
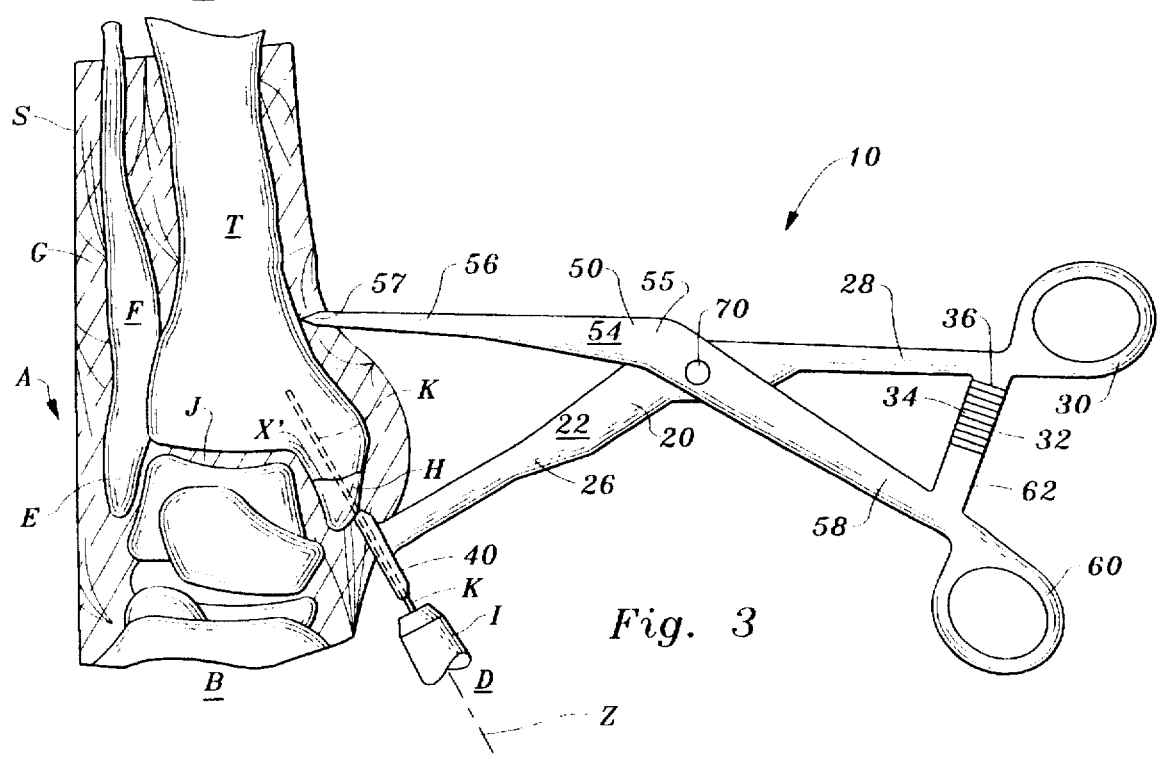
FIG. 3 is a front elevation view of that which is shown in FIG. 2 with the reduction clamp of this invention precisely positioned and in use repairing the lower tip of the tibia of the patient.

With particular reference to FIGS. 2 and 3, details of the reference leg 50 of the reduction clamp 10 are provided. The reference leg 50 is a rigid elongate construct somewhat similar in size and shape to that of the guide leg 20. The reference leg 50 is preferably formed from the same material as that which forms the guide leg 20. The reference leg 50 includes an inner side 52 (FIGS. 4 and 5) and an outer side 54. The inner side 52 and outer side 54 are generally planar and parallel to each other. The reference leg 50 is generally linear but does include a curve 55 at a central location there along. The curve 55 defines a transition between a reference end 56 and a handle end 58 of the reference leg 50. Both the reference end 56 and the handle end 58 are linear and diverge in orientation by a curve angle β. Preferably, the curve angle β measures 150°.

While the bend 25 and curve 55 are preferred, the legs 20, 50 could be configured fully linearly without the bend 25 and curve 55 or with modified angles α, β. The bend 25 and curve 55 enhance the usefulness of the clamp 10 by rotating the handle loops 30, 60 to a position closer to the drill guide 40.

The reference end 56 has a sharpened tip 57 on an end thereof most distant from the curve 55. The sharpened tip 57 is sufficiently sharp to allow the sharpened tip 57 to penetrate into a surface of a bone fragment when force is applied through the sharpened tip 57 from the reference end 56 of the reference leg 50. The sharpened tip 57 extends away from the reference leg 50 generally along a long axis of the reference end 56 thereof. Thus, the sharpened tip 57 does not point toward the drill guide 40 and provide an opposing force with the drill guide 40, except to the extent that friction forces exist between the sharpened tip 57 and the bone adjacent thereto.

A handle end 58 of the reference leg 50 has a handle loop 60 at a tip thereof opposite the curve 55. The handle loop 60 is preferably configured similarly to the handle loop 30 of the guide leg 20. Alternatively, either the handle loop 60 or the handle loop 30 can be particularly configured to receive the thumb of a medical professional while the other of the handle loop 30 and the handle loop 60 can be configured to receive the index finger or other of the medical professional.

The second clamp tab 62 extends away from the handle end 58 of the reference leg 50 and toward the first clamp tab 32 of the guide leg 20. The second clamp tab 62 includes a plurality of second clamp teeth 66 (FIGS. 1, 4 and 5) on an interior side 64 thereof. The interior side 64 is parallel to and faces in a common direction with the inner side 52 of the reference leg 50. Both the first clamp tab 32 and the second clamp tab 62 are configured similarly and extend toward each other.

Because the reference leg 50 and guide leg 20 are pivoted together through the pivot 70, the first clamp tab 32 and second clamp tab 62 can be brought closer together or moved further apart by pivoting of the guide leg 20 and reference leg 50 with respect to each other. The first clamp teeth 36 and second clamp teeth 66 are oriented such that they face each other when the first clamp tab 32 and second clamp tab 62 overlap each other. The clamp teeth 36, 66 are biased such that when they are brought adjacent each other, the teeth 36, 66 lock together. If additional closing pressure is provided between the two handle loops 30,60, the first clamp tab 32 and second clamp tab 62 can be brought still closer together and the teeth 36, 66 can readily reengage and lock at the closer position. However, the teeth 36, 66 are biased such that the teeth 36, 66 do not allow the reduction clamp 10 to be loosened readily when force is applied pushing the handle loops 30, 60 away from each other. Thus, the reduction clamp 10, through action of the clamp tabs 32, 62, tends to lock in position once the tabs 32, 62 are oriented adjacent each other.

The material forming the guide leg 20 and reference leg 50 is sufficiently flexible to allow the handle end 28 of the guide leg 20 and the handle end 58 of the reference leg 50 to be pivoted slightly away from each other and out of a plane in which the legs 20, 50 reside to unlock the clamp tabs 32, 62 from each other when desired. However, this motion is sufficiently unusual to prevent the reduction clamp 10 from becoming unlocked accidentally. This flexibility between the handle end 28 of the guide leg 20 and the handle end 58 of the reference leg 50 can similarly be provided by providing a slight amount of play in the pivot 70 to allow the guide leg 20 and reference leg 50 to be pivoted out of the legs 20, 50 common plane. Typically, except when the clamp tabs 32, 62 are to be disengaged from each other, the guide leg 20 and reference leg 50 remain adjacent a common plane at all times.

While the clamp tabs 32, 62 have been described in detail, various different clamping configurations are known for surgical reduction clamps and could be configured on the reduction clamp 10 of this invention. The clamping means is provided to secure the relative positions of the guide leg 20 and reference leg 50 and particularly the drill guide 40 and sharpened tip 57 of the reference leg 50 once the desired position is achieved for the bone fragments to be reattached. The clamping means thus assists the medical professional in restraining motion of the bone fragments during the drilling procedure.

Having thus described the various different structural features of the reduction clamp 10, a variety of different inter-relationships between the different portions of the reduction clamp 10 are now described. The guide end 26 of the guide leg 20 and the reference end 56 of the reference leg 50 are both generally linear and are coupled together through the pivot 70. The guide end 26 and reference end 56 are both oriented in a generally common plane. However, the guide end 26 and reference end 56 are not parallel to each other. Rather, they diverge from each other by a variable jaw angle γ (FIG. 1). The jaw angle γ is adjustable as the guide leg 20 is pivoted with respect to the reference leg 50. However, the range of angles for the jaw angle γ vary from 15° to 60°.

The drill guide 40 (FIG. 2) is preferably oriented perpendicular to a long axis of the guide end 26 of the guide leg 20. However, the exact angle with which the alignment axis Z relates to the long axis of the guide end 26, referred to as the guide angle δ, could have any of a variety of different measurements. However, the guide angle δ is preferably 90° to provide the drill guide 40 perpendicular to the guide end 26. Regardless of the guide angle δ, the drill guide 40 is preferably fixed with relationship to the guide end 26 such that the guide angle δ is constant.

Preferably, the reference end 56 of the reference leg 50 is slightly shorter than the guide end 26 of the guide leg 20. This length difference, as well as the jaw angle γ having a measurement greater than 0°, causes the drill guide 40 to have its central alignment axis Z pass beyond the sharpened tip 57 (FIG. 2) of the reference end 56, but in a common plane with the reference end 56. This angle of divergence λ by which the alignment axis Z of the drill guide 40 extends beyond an imaginary line extending from the drill guide 40 to the sharpened tip 57 of the reference end 56 is always greater than 0°. Thus, the sharpened tip 57 of the reference end 56 of the reference leg 50 does not provide opposition directly for the the drill guide 40 and guide leg 20. Rather, the reduction clamp 10 relies upon friction between the sharpened tip 57 and the bone fragment to which the sharpened tip 57 is oriented to provide the necessary force to hold that bone fragment in position during the drilling process.

The divergence angle λ preferably measures between 15° and 45°, having a preferable measurement of approximately 20°. This divergence angle λ measurement is particularly useful for repair of a lower tip H of a tibia T fracture to provide the orientation of a bone reattachment structure where desired and avoiding areas such as a joint region J below the tibia T. For different surgery environments, the divergence angle λ could be adjustable to provide the alignment axis Z at a position which is desired for maximum effectiveness of the reduction clamp 10.

Because the drill guide 40 is generally perpendicular to the long axis of the guide end 26 of the guide leg 20, and the guide angle δ measures 90°, basic right angle trigonometry can be utilized to establish relationships between the various angles of the reduction clamp 10 and the lengths of the guide end 26 and reference end 56. With reference to FIG. 1, the guide end 26 length can be identified by reference dimension N, the reference end 56 length can be identified by reference dimension M, a separation length L is provided from the sharpened tip 57 to the alignment axis Z along the long axis of the reference end 56, and a penetration length P from the long axis of the guide end 26, along the alignment axis Z to the point where the alignment axis Z intersects the long axis of the reference end 56. The various lengths P, N, L, M are related as follows:

cos γ=N/(L+M)
sin γ=P/(L+M)
tan γ=P/N
$p^2 N^2=(L+M)^2$.

By use of these trigonometric relationships, it is possible to calculate details such as the separation length L and penetration length P and angle γ when the reference end length M and the guide end length N are known and when one other factor is known such as the jaw angle γ, the separation length L or the penetration length P. Such trigonometric relationships are then useful in surgery planning to ensure that the alignment axis Z for a location of the bone fixation material are oriented as desired and to predetermine a penetration depth to be utilized for the bone fixation structure.

In use and operation, the integrated surgical reduction clamp and drill guide 10 can be used in the following manner to perform a pair of common ankle A surgeries (FIGS. 2–5). However, with some modification various other different orthopedic fracture repair surgeries could similarly be performed with this reduction clamp 10. The first fracture repair surgery involves repair of a fracture of the lower tip H of the tibia T away from a remaining portion of the tibia T (FIGS. 2 and 3). As shown in FIG. 2, the tibia T and lower tip H are separated apart by a fracture X. The tibia T extends vertically from the leg C down to the foot B at a region generally referred to as the ankle A. The lower tip H and tibia T are shown oriented within the skin S and surrounded by flesh G.

Before utilization of the reduction clamp 10, various commonly known surgery preparation procedures are performed such as anesthetization of the patient, cleansing of the ankle A, and immobilization of the leg C and foot B along with the ankle A, as much as possible. Appropriate incisions are then made to reveal the portions of the tibia T and lower tip H which are to be repaired. For instance, an incision can be made adjacent the fracture X and adjacent the sharpened tip 57 to allow the surgeon to effectively apply the sharpened tip 57 against the tibia T at a desired reference point. The sharpened tip 57 is then applied against the tibia T with sufficient force to cause the sharpened tip 57 to penetrate the tibia T slightly and prevent slippage of the reference end 56 of the reference leg 50 (FIG. 3).

The reduction clamp 10 is then closed by drawing the handle loop 30 and handle loop 60 toward each other until the outlet end 48 of the drill guide 40 impacts the lower tip H and draws the lower tip H closed against the tibia T (FIG. 3). Because the outlet end 48 has a sharpened rim 49, the drill guide 40 does not readily slip once it contacts the tip H. The first clamp tab 32 and second clamp tab 62 interface with each other, locking the guide leg 20 and reference leg 50 into fixed relationship with each other. Because the reference leg 50 is shorter than the guide leg 26 and because the drill guide 40 is generally perpendicular to a long axis of a guide end 26, the drill guide 40 provides the alignment axis Z at a divergence angle λ (FIG. 1) which ensures appropriate orientation of the alignment axis Z. Specifically, the alignment axis Z preferably remains within the tibia T and does not enter the joint region J or other portions of the flesh G in which the bone fixation structure is not to be located.

Various different bone fixation techniques are known in the art, including wire K, screws, pins, rivets and other attachment devices. While wire K is shown in FIGS. 2–5, it is understood that the wire K could be replaced with a screw or other bone fixation. When wire K is utilized, one type of wire K which has been found to be effective is referred to in the medical arts as "K-wire" and is unique in that it is self tapping and is configured with appropriate cutting surfaces at a tip thereof such that when the K-wire is attached to a drill D through a chuck I, the K-wire can penetrate into the bone.

In this application, the wire-K abuts the tibia T and simultaneously drills a hole for location of the wire K and also draws the wire K into the hole which is made. Thus, a one-step wire K insertion process is provided. If pins or screws are utilized, generally a two step process is involved where first a drill bit is utilized to drill a hole and second a pin or screw is screwed into the hole formed by the drill bit.

The drill guide 40 is preferably cylindrical to totally support location of the wire K at the desired position. However, as an alternative to this cylindrical form of the drill guide 40, it is possible that the drill guide 40 could provide only partial support for the wire K by being arcuate or having a square or other cross-sectional shape. The drill guide 40 has a long axis which defines the alignment axis Z upon which the wire K is to be aligned.

Once the reduction clamp 10 is in place adjacent the tibia T and lower tip H with the lower tip H drawn against the tibia T, the fracture X' is closed and ready for reattachment. The drill D is then utilized with a wire K or drill bit extending from a chuck I of the drill D. The wire K is passed through the inner cylindrical surface 44 of the drill guide 40 and then the drill D is activated, causing the wire K to penetrate into the lower tip H, across the fracture X' and into the tibia T (FIG. 3). If desired, multiple wires K can be utilized at adjacent positions to securely reattach the lower tip H to the tibia T.

Once the wire K has been appropriately positioned, the wire K is cut and an end bent adjacent the lower tip H so that none of the wire K is exposed and the surgical sight can be closed. Not only does the reduction clamp 10 hold the lower tip H and tibia T in the appropriate relative position, but the reduction clamp 10 also provides the drill guide 40 for support of the drill D and wire K and also provides the appropriate divergence angle λ for the orientation of the wire K alignment axis Z.

Similarly, and with reference to FIGS. 4 and 5, the reduction clamp 10 can be utilized to reattach the lower end E of the fibula F when the fibula F is fractured such as along a fracture line Y. Initially, after preparation of the ankle A for the surgery process, the reduction clamp 10 is brought into a position so that the sharpened tip 57 of the reference leg 50 can be secured against the fibula F. Then, the handle loops 30, 60 are drawn together until the outlet end 48 of the drill guide 40 impacts the lower end E and draws the lower end E adjacent the fibula F to close the fracture Y'. Because the outlet end 48 includes the sharpened rim 49, both the reference end 56 and guide end 26 are configured to discourage slippage of the reduction clamp 10 away from the lower end E and fibula F. Once the fracture Y' has been closed and the clamp tabs 32, 62 have locked the reference leg 50 and guide leg 20 into the appropriate relative position, the drill D and wire K are utilized to insert the wire K along the wire alignment axis Z', through the drill guide 40, through the lower end E, across the fracture Y' and into the fibula F.

While the utilization of the reduction clamp 10 in various different ankle a surgeries has been described with respect to wire K, it is understood that the similar procedure would be utilized with a drill bit and screw passing through the drill guide 40 for alignment thereof while the reduction clamp 10 holds the various different portions of the fractured bones in their appropriate position for reattachment.

Moreover, having thus described the invention it is understood that various different modifications to the invention could be resorted to without departing from the scope of this invention as described herein above and as claimed herein below. For instance, the specific angular measurements provided herein could be adjusted somewhat without drastically altering the effectiveness of this reduction clamp 10. Also, the configuration of the handle loops 30, 60 and clamp tabs 32, 62 could take on a variety of different configurations for user convenience and user preference without affecting the overall performance of the reduction clamp 10.

What is claimed is:

1. An integrated surgical reduction clamp and drill guide for simultaneously supporting adjacent fragments of a fractured bone together and aligning the placement of a fractured bone fixation structure, comprising:

a reference leg having a tip;

a guide leg having a guide means to guide the orientation of a fractured bone fixation structure along an alignment axis to a desired location passing through the fragments of the bone on opposite sides of the fracture and through the fracture, wherein said guide means includes a hollow cylinder attached to an end of said guide leg, said hollow cylinder having a central axis collinear with said alignment axis and having an inner cylindrical surface with a diameter not less than a diameter of the bone fixation structure, such that said bone fixation structure can pass through said hollow cylinder;

a pivot interposed between said reference leg and said guide leg, said pivot including means to resist translation between said reference leg and said guide leg and means to allow rotation between said reference leg and said guide leg;

said reference leg having a length from said pivot to said tip which is shorter than a length of said guide leg from said pivot to said guide means, such that the guide means and said tip of said reference leg are not fully opposing.

2. The reduction clamp and drill guide of claim 1 wherein said guide means is linearly aligned with the desired location along said alignment axis which extends past a location of said tip, said line oriented in a common plane with said reference leg and said tip, said tip remaining spaced from said alignment axis.

3. The reduction clamp and drill guide of claim 1 wherein a hand grasping means is provided on said reference leg and on said guide leg, each said grasping means oriented on the same side of said pivot and on a side of said reference leg opposite said tip and on a side of said guide leg opposite said guiding means.

4. The reduction clamp and drill guide of claim 3 wherein said tip of said reference leg is sharpened to a point having sufficient sharpness to penetrate a surface of a bone fragment somewhat when linear force is applied to said tip from said reference leg, and wherein said hollow cylinder of said guide means includes an inlet end and an outlet end, said outlet end oriented closer to said tip of said reference leg than said inlet end, said outlet end having a sharpened rim exhibiting sufficient sharpness to allow said sharpened rim to penetrate a surface of a bone fragment somewhat when force is applied to said outlet end of said guide means through said guide leg.

5. The reduction clamp and drill guide of claim 4 wherein said reference leg and said guide leg include means to clamp to each other in a manner restricting rotation between said reference leg and said guide leg, and maintaining compressive force between said tip of said reference leg and said outlet end of said guide means of said guide leg, such that said tip and said outlet end of said guide means can act as a clamp holding adjacent pieces of bone fragments to be rejoined in positions adjacent each other.

6. The reduction clamp and drill guide of claim 5 wherein said alignment axis along which said guide means is linearly aligned diverges from an imaginary line extending from said guide means to said tip of said reference leg by a divergence angle between fifteen degrees and forty-five degrees, such that said reduction clamp and drill guide can orient a bone fixation structure in the correct position to be useful in ankle surgery for humans where fractured portions of a lower end of a tibia or a lower end of a fibula are to be reattached.

7. A non-opposing surgical reduction clamp and drill guide for supporting fractured bone fragments during orthopedic bone repair surgery, comprising:

a reference leg having a tip;

a guide leg having a means to linearly guide the orientation of a drill-driven fractured bone fixation device to a desired location oriented along an alignment axis of said guide means, wherein said guide means includes a hollow cylinder fixed to an end of said guide leg, said hollow cylinder having a bore extending from an inlet end to an outlet end, said outlet end oriented closer to said tip of said reference leg than said inlet end;

a means to couple said reference leg and said guide leg together in a manner allowing a pivoting movement of the guide leg and reference leg relative to each other about a pivot point;

said alignment axis oriented in a plane including said tip of said reference leg, but diverging from the location of said tip such that a linear distance from said pivot point to said alignment axis is greater than a linear distance from said pivot point to said tip of said reference leg.

8. The clamp of claim 7 wherein said tip of said reference leg is sharpened a sufficient amount to allow said tip to penetrate into a surface of a bone when said tip is oriented adjacent the bone and force is applied from said reference leg to said tip.

9. The clamp of claim 8 wherein said guide leg includes a means to grasp the guide leg with a hand on a side of said coupling means opposite said guide means, wherein said reference leg includes a hand grasping means on a side of said reference leg opposite said sharpened tip, and wherein said clamp includes a means to clamp said reference leg into fixed position with respect to said guide leg in a manner preventing rotation and translation between said reference leg and said guide leg.

10. The clamp of claim 9 wherein said alignment axis of said guide means diverges from a line extending from said linearly guiding means to said tip of said reference leg by a divergence angle measuring between fifteen degrees and forty-five degrees.

11. The clamp of claim 10 wherein said divergence angle has a measurement between twenty degrees and forty degrees when a jaw angle at which said reference leg diverges from said guide leg has a measurement of thirty degrees.

12. The clamp of claim 7 wherein said outlet end of said hollow cylinder includes a sharpened rim, said sharpened rim having sufficient sharpness to penetrate into a surface of a bone when force is applied to said sharpened rim from said guide leg.

13. A method for repairing a bone fracture where the fracture is non-parallel with many adjacent surfaces of the bone, such that an opposing reduction clamp cannot be used to hold fragments of the bone adjacent the fracture together, including the steps of:

identifying first and second fragments of a bone which have been fractured apart and are to be rejoined together, at least one of the fragments not having a nearby surface parallel to the fracture against which an opposing reduction clamp can be used to close the fragments into contact with each other;

providing a non-opposing surgical reduction clamp and drill guide including:

a reference leg having a tip;

a guide leg having a guide means to guide the orientation of a fixation device along an alignment axis to a desired location passing through fragments of the bone on opposite sides of a fracture and through the fracture;

a pivot interposed between the reference leg and the guide leg, the pivot including means to resist translation between the reference leg and the guide leg and means to allow rotation between the reference leg and the guide leg;

the reference leg having a length from the pivot to the tip which is shorter than a length needed to extend the tip to a region intersecting the alignment axis, such that the guide means and the tip of the reference leg are not fully opposing;

placing the tip of the reference leg against a surface of the first bone fragment with the tip penetrating the surface;

positioning the guide means against a surface of the second bone fragment;

rotating the reference leg and guide leg about the pivot until the first bone fragment and the second bone fragment are adjacent each other;

orienting the bone reattachment structure adjacent the guide means; and inserting the bone fixation device through the second bone fragment, across the fracture and into the first bone fragment while aligned by the guide means.

14. The method of claim 13 wherein said bone fixation device utilized in said orienting step is a pin which is configured to be self-tapping within bone structures.

15. The method of claim 13 wherein a drilling step is provided before said orienting step, said drilling step including the steps of locating a drill bit within the guide means, inserting the drill bit into the second bone fragment, across the fracture and into the first bone fragment while the drill bit is rotating, and removing the drill bit from the first bone fragment and the second bone fragment.

16. The method of claim 15 wherein said bone reattachment structure of said orienting step is a pin having sufficient length to extend through said second bone fragment, across the fracture and into the first bone fragment.

17. The method of claim 16 wherein said providing step includes the step of forming the guide means as a hollow cylinder having a bore of constant circular cross-section extending from an inlet end to an outlet end, the cylinder aligned with the alignment axis which extends past a location of the tip of the reference leg and in the same plane as the tip of the reference leg.

18. The method of claim 17 wherein said providing step further includes the steps of providing the tip of the reference leg with sufficient sharpness to penetrate the surface of a bone somewhat, wherein the outlet end of the hollow cylinder of the guide means includes a sharpened rim having sufficient sharpness to penetrate the surface of a bone somewhat, providing both the reference leg and the guide leg with hand grasping means through which a user can adjust the relative positions of the reference leg and the guide leg, providing a means to clamp the reference leg and the guide leg into fixed position relative to each other while resisting displacement or rotation there between, and providing a divergence angle between the alignment axis along which the hollow cylinder extends and an imaginary line extending from the drill guide to the tip of the reference leg having an angle measuring between fifteen degrees and forty-five degrees.

* * * * *